(12) United States Patent
Lovatt

(10) Patent No.: US 6,169,057 B1
(45) Date of Patent: Jan. 2, 2001

(54) USE OF TRYPTOPHAN AND ANALOGS AS PLANT GROWTH REGULATORS

(75) Inventor: Carol J. Lovatt, Riverside, CA (US)

(73) Assignee: The Regents of the University of California, Oakland, CA (US)

( * ) Notice: Under 35 U.S.C. 154(b), the term of this patent shall be extended for 0 days.

(21) Appl. No.: 08/923,351

(22) Filed: Sep. 4, 1997

(51) Int. Cl.$^7$ .......................... A01N 43/36; A01N 43/00
(52) U.S. Cl. .................. 504/284; 504/138; 504/136; 504/166
(58) Field of Search .................. 504/138, 284, 504/136, 166

(56) References Cited

PUBLICATIONS

Crozier et al. (Canadian J. of Botany, vol. 48, 1970, pp. 867–877).*
Shiozaki et al (CA 123:3277 abstract of Engei Gakki Zasshi (1995), 63(4), 703–10).*
Rekoslavskaya, N. I. (CA 104:183376 abstract of Biol. Plant. (1986), 28(1), 62–67).*
Osakaja, V. (CA 77:97569, abstract of Mikroorganizmy Rast. (1972), 5, 137–49).*
Kato et al. (CA 85:88519 abstract of JP 51029229, 1976).*
Harry R. Carns (Ann. Rev. Plant Phys. vol. 17, (1966), p. 295–314).*
Koto, Toru (CA 108:145463 abstract of JP 62265208, 1987).*
Arshad et al. (CA 124:48251 abstract of Proc. Plant Growth Regul. Soc. Am. (1994), 21st, 75–88).*
Sarwar Muhammad et al. (CA 120:294327 abstract of Plant Soil (1994), 160(1), 97–104).*
Libbert et al.; "The influence of epiphytic bacteriae on auxin metabolism"; *Planta* (Berl.) 68:327–334 (1966).
Libbert et al.; "Interactions between Plants and Epiphytic Bacteria Regarding Their Auxin Metabolism: V. Isolation and Identification of the IAA–Producing and –Destroying Bacteria from Pea Plants"; *Physiologia Plantarum* vol. 22 (1969), pp. 51–58.
Libbert et al.; "Interactions between Plants and Epiphytic Bacteria Regarding Their Auxin Metabolism: VI. The Influence of the Epiphytic Bacteria on the Content of Extractable Auxin in the Plant"; *Physiologia Plantarum* vol. 22 (1969), pp. 432–439.
Libbert et al.; "Interactions between Plants and Epiphytic Bacteria Regarding Their Auxin Metabolism: IX. The Influence of the Epiphytic Bacteria on the Auxin Production from Tryptophan Applied to Corn Shoots and Coleoptiles"; *Physiologia Plantarum* vol. 22 (1969), pp. 432–439.

* cited by examiner

Primary Examiner—Sabiha N. Qazi
(74) Attorney, Agent, or Firm—Townsend and Townsend and Crew LLP

(57) ABSTRACT

The invention provides methods and compositions for improving crop yield. The methods involve application of tryptophan compounds to the canopy of plants. The compositions comprise tryptophan compounds for use with the methods of the invention.

22 Claims, 2 Drawing Sheets

USE OF TRYPTOPHAN AND ANALOGS AS PLANT GROWTH REGULATORS

BACKGROUND OF THE INVENTION

1. Field of the Invention

The present invention relates to methods of improving productivity of crop plants. In particular it relates to the application of compositions comprising tryptophan and/or tryptophan derivatives to plants.

2. Background of the Invention

Plant hormones (i.e., plant-growth regulators) play an important role in controlling plant growth and development. These compounds are useful for altering a plant's life processes or structure in some beneficial way so as to enhance yield, improve quality or facilitate harvesting. Growth-regulating compounds which are produced by plants are generally classified as one of four types of hormone: auxins, gibberellins, cytokinins and inhibitors. Many synthetic compounds mimic the activity characteristic of natural plant-growth regulators.

One class of plant hormone, auxins, and their synthetic mimics are of particular interest. Auxin-like activity is known to affect a number of plant processes, such as cell division, rooting at the basal end of shoots, shoot elongation, apical dominance, phototropic responses and control of abscission of organs such as buds, flowers, fruits, leaves and the like. Plant-growth regulators with auxin-like activity comprise an important class of chemicals for use in agriculture. As of 1994, there were approximately 29 compounds with auxin-like activity approved for agricultural use worldwide. Of these compounds, 21 were approved for use in the United States (KIRK-OTHMER ENCYCLOPEDIA OF CHEMICAL TECHNOLOGY, 4th Ed., Kroschwitz et al., Eds., John Wiley & Sons, New York, 1994). A particularly widely used synthetic auxin is 2,4-dichlorophenoxyacetic acid (2,4-D). Among its many uses, 2,4-D is sprayed on the foliage of citrus trees in California and Florida (also in citrus growing countries such as Israel, Spain, Morocco, South Africa, etc.) to prevent preharvest fruit drop and to increase fruit size.

The agricultural application of exogenous chemicals to food crops is coming under increased scrutiny by many segments of society including the agricultural industry, advocates for agricultural laborers, environmental groups and consumers. In the United States, agricultural industry concerns stem from the fact that plant growth regulators must be officially registered with the Environmental Protection Agency (EPA) before they can be used or sold. Additionally, as plant-growth regulators are often applied closer to harvest than are pesticides, the actual practical requirements for their safety are more stringent.

The screening process associated with the official registration is both time-consuming and expensive. This process includes evaluation of a plant-growth regulator's safety hazards to humans, the environment and nontarget species. Further, acute and chronic toxicity must be determined. The agricultural industry shoulders a portion of the costs of the preregistration program in higher prices. Further, the industry typically bears part of the financial burden for reregistering the compound for a particular use. For example, the California citrus industry paid approximately two million dollars to effect the reregistration of 2,4-D as a preharvest fruit drop inhibitor. In addition to these financial concerns, the potential toxicity of synthetic plant-growth regulators raises additional concerns regarding the safety of their use.

The concerns of environmental groups, advocates for agricultural laborers and consumers arise from the potential toxicity of plant-growth regulators. For example, auxin mimics such as 2,4-D and related phenoxy acids have moderately acute toxicity and are moderate in their local effects upon the skin or eyes (Gehring et al. *Ecol. Bull.* (Stockholm) 27:122 (1978)). Results of cytogenic studies in Sweden indicate that, in practice, 2,4-D constitutes a cytogenic hazard to man (Jenssen et al. *Chem. Biol. Interaction* 14:291 (1976)). Additionally, 2,4-D has been found to exhibit central nervous system toxicity (Elo et al. *Acta Pharmacol. Toxicol.* 41:280 (1977)).

In light of their utility in preventing preharvest fruit drop and increasing fruit size, coupled with the expense of registration, reregistration and the potential toxicity of auxin mimics, alternatives to the use of synthetic auxins are being actively sought.

The application to plants and soils of natural auxins and natural auxin precursors is a particularly promising alternative to the use of synthetic auxin mimics. For instance, L-tryptophan has been reported to serve as precursor for the microbial formation of indole-3-acetic acid (IAA) (see, e.g., Arshad and Frankenberger *Plant Soil* 133:1–8 (1991)). Further, the synthesis of IAA upon application of tryptophan to soil has been shown to promote plant growth. For instance, growth of Douglas fir was increased by application of tryptophan and inoculation with a fungus capable of producing IAA from tryptophan (Frankenberger and Poth *Appl. Environ. Microbiol.* 53:2908–2913 (1987)). When tryptophan was applied to soils under aseptic conditions (i.e., steam-sterilized soil), L-TRP conversion to IAA was not observed (Martens and Frankenberger *Soil Science* 155:263–271 (1993)). Thus, it was concluded that the conversion of tryptophan to IAA was a microbe-mediated process.

Whether intact plants, in the absence of the soil microorganisms, are capable of converting tryptophan to IAA remains an open question which numerous experiments have attempted to answer. In spite of preliminary evidence that excised segments of plant are capable of converting tryptophan to IAA (see, e.g., Kutáček and Kefeli *Biologia Plantarum* (Praha) 12:145–158 (1970) and Bertling and Lovatt, Annual Meeting of the American Society for Horticultural Science, Aug. 7–10, 1994, *HortScience* 29, Abstract #752 (1994)), the question still remains whether the delivery to intact plants of tryptophan would result in auxins being synthesized to an extent sufficient to give rise to an auxin response in the plant.

When tryptophan is administered to intact, growing plants, yield data points to an absence of uptake or conversion of tryptophan. For example, in an experiment with radish plants which compared the effects of the foliar application of tryptophan to whole plants with the application of tryptophan to the soil, the application of tryptophan to the soil was found to promote radish growth. In contrast, the foliar application of tryptophan in dosage amounts between $10^{-2}$ M and $10^{-10}$ M had no effect on the growth of the radishes. Thus, it was concluded that tryptophan was not taken up by intact leaves and that the site of entry for tryptophan was through the soil and root (Frankenberger et al. *Plant Soil* 129:235–242 (1990)).

A need exists for inexpensive, non-toxic and effective methods and compositions for improving crop productivity. If such methods and compositions were also as effective as the currently used treatment of plants with 2,4-D they would indeed represent a significant advance over the current state of the art. Quite surprisingly, the present invention provides such methods and compositions.

SUMMARY OF THE INVENTION

The present invention provides methods of improving productivity in crop plants by applying an effective amount of tryptophan and tryptophan derivatives to crop plants. Increased productivity can be measured by a number of parameters. For instance, the plants will typically show increased yield or synchronization of fruit set. Of particular interest is the use of the method and composition of the invention to prevent preharvest fruit drop.

The advantages of the present invention over prior methods using synthetic auxin mimics include:

(1) tryptophan, being one of the 21 essential amino acids, is a benign compound, whereas synthetic auxins such as 2,4-D are toxic and have mutagenic and carcinogenic potential;

(2) although the EPA has not yet refused to reregister synthetic auxins such as 2,4-D, produce which is treated with such compounds is increasingly being rejected by consumers in Europe, Pacific Rim countries and the United States; and (3) tryptophan is significantly less expensive to produce than are synthetic auxin mimics.

Thus, in one aspect, the present invention provides a method of inducing an auxin response in a living plant, the method comprising applying to the canopy of a plant an amount of a compound effective to induce the auxin response, wherein the compound has a structure according to Formula I

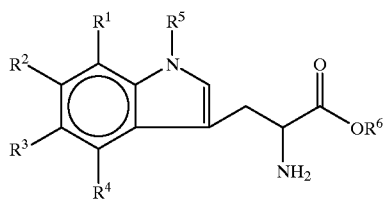

(I)

wherein $R^1$, $R^2$, $R^3$ and $R^4$ are independently members selected from the group consisting of hydrogen, hydroxyl, alkoxy, amino, halogen and $C_1$–$C_6$ alkyl; and $R^5$ and $R^6$ are independently members selected from the group consisting of hydrogen, $C_1$–$C_6$ alkyl, $C_1$–$C_6$ alkyl substituted with hydroxyl, polyalkylene glycol and substituted polyalkylene glycol.

In a second aspect, the invention is a method of controlling abscission in a living plant, the method comprising applying to the canopy of the plant an amount of tryptophan effective to control abscission.

In a third aspect, the invention provides a method for decreasing acidity in citrus fruit comprising applying to the canopy of a plant an amount of a tryptophan compound effective to reduce the acidity, wherein the tryptophan compound has a structure according to Formula I.

In still a further aspect, the invention provides a composition for application to crop plants, the composition comprising a productivity enhancing effective amount of a compound having a structure

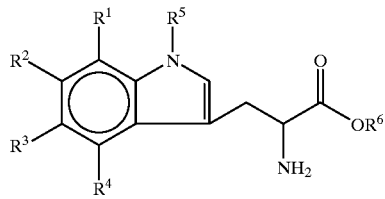

wherein $R^1$, $R^2$, $R^3$ and $R^4$ are independently members selected from the group consisting of hydrogen, hydroxyl, alkoxy, amino, halogen and $C_1$–$C_6$ alkyl; and $R^5$ and $R^6$ are independently members selected from the group consisting of hydrogen, $C_1$–$C_6$ alkyl, $C_1$–$C_6$ alkyl substituted with hydroxyl, polyalkylene glycol and substituted polyalkylene glycol.

The present invention provides methods of improving productivity in crop plants and compositions to be used in conjunction with those methods. Additional objectives and advantages will be set forth in the description which follows, and in part will be apparent from this description, or can be learned by practice of the invention. The objects and advantages of the invention can be realized and obtained by means of the methods and compositions particularly pointed out in the appended claims.

DETAILED DESCRIPTION OF THE INVENTION AND PREFERRED EMBODIMENTS

Definitions

Figure 1:
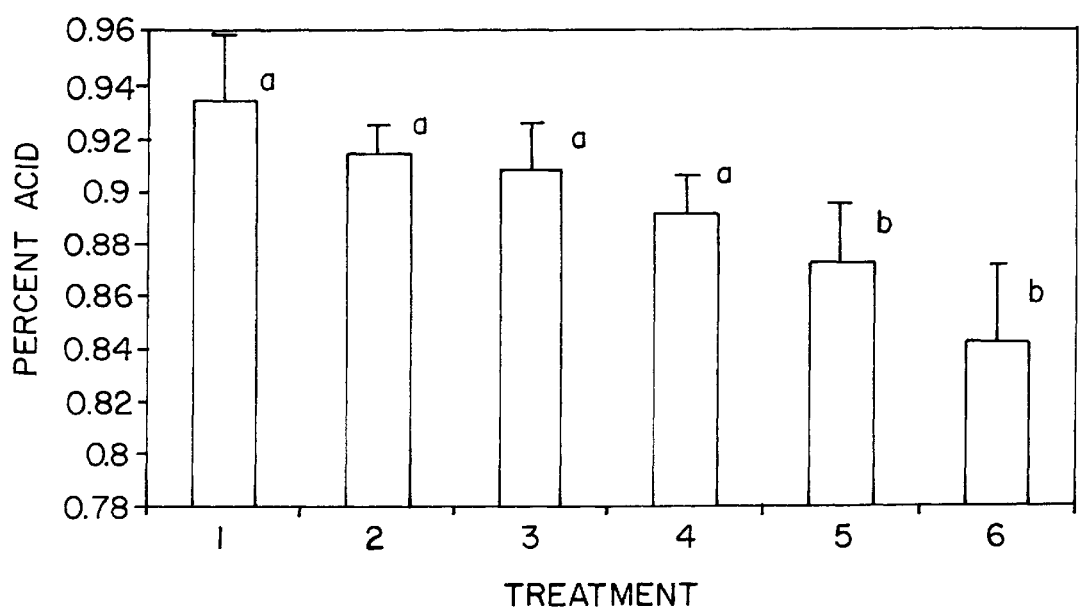
FIG. 1 shows the effect of foliar-applied DL-tryptophan on percent acid of the juice at harvest. 1) control—no tryptophan; 2) $10^{-6}$ M tryptophan applied at fb; 3) $10^{-8}$ M tryptophan applied at fb; 4) $10^{-10}$ M tryptophan applied at fb; 5) $10^{-8}$ M tryptophan applied 2 was after fb; 6) $10^{-10}$ M tryptophan applied at fb+every 2 weeks for 10 weeks. (fb=full bloom). Error bars indicate the SE of the mean for 5 replicates for treatment 1; 6 replicates for treatments 2, 3, 5, and 6; and 8 replicates for treatment 5. The means were separated at p=0.10 using pairwise t-test.

The terms used herein are defined as follows:

"Auxin response" refers to a change in the timing and/or extent of one or more auxin-sensitive plant physiological processes following treatment of the plant with an auxin, an auxin mimic or an auxin precursor. An "auxin response" can be used to induce or otherwise control processes such as cell elongation, rooting of cuttings, abscission, apical dominance, prevent suckering, fruit set, total yield of fruit, size of fruit and the like.

"Abscission" refers to the loss off of organs such as leaves, flowers, fruits or other plant parts as a result of separation of the organ from the plant stem. Typically, this occurs as a result of dissolution of the abscission layer at the base of the organ, such as the leaf petiole.

"Productivity enhancing," as used herein, refers to a class of plant responses which are induced by the application of a tryptophan compound of the invention to the canopy of a plant. The induced responses are characterized by an enhancement in a desirable characteristic of the plant such as, for example, an increased total yield (e.g., as measured by total weight of the desired plant organ, such as fruit, roots, tubers, leaves and the like), increased size of fruit (e.g., g/fruit) or other organ, increased synchronization of fruit set, simplification of harvest (e.g., thinning of leaves prior to harvest and synchronization of ripening), timing of harvest (e.g., reduced acidity in citrus allows earlier harvest) and enhanced flavor. Other parameters commonly used to measure the productivity of a crop plant will be known to those of skill in the art.

"Effective amount" is an amount of a tryptophan compound of the invention which is sufficient to induce the desired auxin response. In general the auxin response will be one which will be "productivity enhancing," as defined above.

"Canopy" refers to any or all of the components of a plant which are above the level of the soil. As such, the canopy consists of, but is not limited to branches, leaves, flowers, buds and fruit.

"Full bloom" refers to a period in a plant's bloom cycle in which >50% of the flower buds are open.

"Alkyl" denotes straight-chain, branched-chain, saturated and unsaturated groups.

"Alkoxy" denotes "alkyl" with an added oxygen atom covalently linking the alkyl group to the remainder of the formula. Straight-chain, saturated groups are preferred for both alkyl and alkoxy.

"Halogen" is used herein to refer to fluorine, bromine, chlorine and iodine atoms.

"Hydroxy" is used to refer to the group —OH.

"Amino" is used to describe primary amines, —NH$_2$, substituted amines (e.g., methyl amines) and their ammonium salts.

"Polyalkylene glycol" is used to describe compounds such as poly(ethylene glycol), poly(propylene glycol), poly(oxyethylene) and copolymers of these glycols.

"Substituted polyalkylene glycols" describes compounds in which the terminus that is not bound to the tryptophan nucleus is substituted with a group such as, but not limited to, a functionalized sorbitan (e.g., poly (oxyethylene) sorbitan-monolaurate, -monostearate, -monopalmitate, -monooleate and -trioleate. In preferred embodiments, the "substituted polyalkylene glycols" are surface active agents.

"Substituted" encompasses both single and multiple substitutions, the latter including multiple substitutions by the same substituent as well as mixtures of different substituents.

The present invention relates to methods of inducing an auxin response in plants. In preferred embodiments, the response is induced in a crop plant. In other preferred embodiments, the auxin response improves crop productivity. In the discussion and examples which follow, tryptophan compounds are shown to be effective in increasing crop yield as measured in total fruit weight. Further, the methods and compositions of the invention are useful in controlling abscission and synchronizing fruit set in plants, as measured in number of fruit per harvest. The tryptophan compounds also increase the size of individual fruit and reduce the amount of acid contained in fruit.

In a first aspect, the invention provides a method of inducing an auxin response in a living plant, the method comprising applying to the canopy of a plant an amount of a tryptophan compound effective to induce the auxin response, wherein the tryptophan compound has a structure according to Formula I

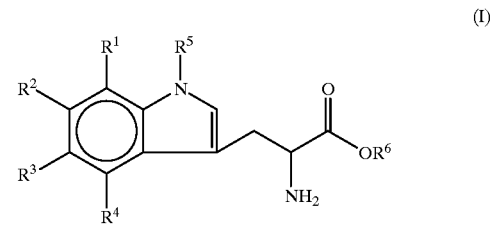

wherein $R^1$, $R^2$, $R^3$ and $R^4$ are independently members selected from the group consisting of hydrogen, hydroxyl, alkoxy, amino, halogen and $C_1$–$C_6$ alkyl; and $R^5$ and $R^6$ are independently members selected from the group consisting of hydrogen, $C_1$–$C_6$ alkyl, $C_1$–$C_6$ alkyl substituted with hydroxyl, polyalkylene glycol and substituted polyalkylene glycol.

In one embodiment, $R^1$, $R^2$, $R^3$ and $R^4$ are independently members selected from the group consisting of hydrogen, alkoxy and halogen;

$R^5$ is a member selected from the group consisting of hydrogen and $C_1$–$C_2$ alkyl substituted with hydroxyl; and $R^6$ is a member selected from the group consisting of hydrogen, $C_1$–$C_2$ alkyl substituted with hydroxyl and polyalkylene glycol.

In another embodiment, $R^1$, $R^2$, $R^3$ and $R^4$ are independently members selected from the group consisting of hydrogen, methoxy and chloro;

$R^5$ is a member selected from the group consisting of hydrogen and $C_1$–$C_2$ alkyl substituted with hydroxyl; and $R^6$ is a member selected from the group consisting of hydrogen and polyalkylene glycol.

In a further embodiment, $R^1$, $R^2$, $R^3$ and $R^4$ are independently members selected from the group consisting of hydrogen and chloro;

$R^5$ is hydrogen; and $R^6$ is a member selected from the group consisting of hydrogen and polyalkylene glycol.

In a presently preferred embodiment, $R^1$–$R^6$ are hydrogen atoms and the compound of Formula I is tryptophan or an acceptable salt thereof. The compounds according to Formula I can be utilized as pure enantiomers or as racemic mixtures of compounds. Thus, it is within the scope of the present invention to use the D,L-racemic mixture of a tryptophan compound or the pure D- or L-isomer. Tryptophan compounds which comprise groups capable of enhancing the efficacy of the compounds are also within the scope of the invention.

Thus, in one embodiment, $R^1$–$R^6$ are groups which enhance the uptake of the agent by the plant. The enhanced uptake can be mediated by a number factors including, for example, increased water solubility of the compound and chemical or physical effects which enhance the permeability of the leaf cuticle and/or epidermis. Thus, in one preferred embodiment the tryptophan compound has surfactant characteristics. In another preferred embodiment, the surfactant characteristics are primarily provided by $R^6$. In this embodiment, $R^6$ is chosen from agents such as polyalkylene glycols and substituted polyalkylene glycols which are known to have surface active properties. The polyalkylene glycol can be linked to the tryptophan nucleus via the carboxyl group using any linkage known in the art including, but not limited to, esters, amides, thioesters and the like. Tryptophan compounds which are derivatized via the carboxyl group are well known to those of skill in the art, as are general methods of modifying amino acid carboxyl groups. Additionally, methods of derivatizing amino acids with polyalkylene glycols are well known in the art.

In other embodiments, $R^1$–$R^6$ are chosen such that the substituent alters the intensity or duration of the auxin response relative to that induced by the parent tryptophan molecule. The tryptophan compounds of this embodiment will typically comprise ring-substituted tryptophan derivatives. An array of ring-substituted tryptophan compounds of the invention are easily accessible to those of skill in the art and many are commercially available. In preferred embodiments, $R^1$–$R^4$ are independently hydrogen, halogen, carboxyl or alkoxy. As many potent synthetic auxins comprise benzene rings derivatized with chloro groups, in a preferred embodiment, one or more of $R^1$–$R^6$ are chloro.

Methods for measuring the intensity and duration of an auxin or auxin-like response in a plant or plant tissue are well known to those of skill in the art. These methods are readily adaptable to assaying the effectiveness of tryptophan compounds in inducing an auxin response. As the effectiveness of a particular tryptophan derivative is dependent on both its potency and the magnitude of its uptake by a plant tissue, these two characteristics of a tryptophan compound are of particular interest.

Several methods of measuring the uptake of small molecules by plant tissues are routinely practiced. One such method involves administering to the plant tissue a compound of interest and a tracer amount of a radioactive derivative of that compound. Following a period of incubation, the tissue is measured for uptake of radioactivity. See, for example, Martens and Frankenberger *Soil Science* 155:263–271 (1993), which is incorporated herein by reference. In an analogous manner, whole plants can be treated with a tryptophan derivative and/or its radioactive analog. Following the treatment, the plant, or portions of the plant, are homogenized, and the radioactivity counted in the homogenate. Alternatively, the radioactive species is extracted from the homogenate and counted. In yet another variation, the homogenate or an extract of the homogenate are submitted to chromatography such as high performance liquid chromatography (HPLC). The introduction of a chromatographic step into the analysis allows the radioactive species to be characterized both in terms of its identity and its degree of radioactivity. Other variations on these basic analytical themes can be routinely and quickly developed by, and will be apparent to, those of skill in the art.

In addition to measuring the degree of uptake by a plant or plant tissue of a tryptophan compound, the effectiveness of a particular tryptophan compound at producing an auxin response can be measured by one or more of several assays which are well known to those of skill in the art. For example, tests which are widely accepted as a measure of auxin-like activity are the Avena straight-growth bioassay and the Avena curvature test (MCGRAW-HILL ENCYCLOPEDIA OF SCIENCE AND TECHNOLOGY, Vol. I, 5th Ed., Parker et al., Eds., New York 1982). Additionally, the tryptophan compounds can be tested for their effectiveness in inducing an auxin response in an intact plant. For example, if the tryptophan compound is intended to improve the fruit set of a particular plant, one would administer the tryptophan compound to a small population of the plant and observe the effectiveness of the derivative in achieving the desired goal.

The methods of the present invention can be utilized to induce auxin responses which have a variety of effects on a number of different plant physiological processes. For example, an auxin response can be used to enhance the rooting of cuttings, induce callus formation in tissue culture and clonal plant propagation. Further an auxin response can be induced to either reduce or retard abscission. In a preferred embodiment, the auxin response inhibits flower and/or fruit abscission, thus, increasing the amount of fruit produced. In another embodiment, the tryptophan compound acts as a thinning agent and gives rise to an auxin response which promotes abscission.

The methods of the present invention are effective at inducing an auxin response in a wide range of plants and plant types. In a preferred embodiment, the plant type is a crop plant. In another preferred embodiment, the plant is a citrus (e.g., orange, lemon, grapefruit, tangerine, lime and citron), avocado or tomato plant. As the method of the present invention affords substantially the same results as treating plants with synthetic auxin mimics such as 2,4-D, it will be apparent to those of skill in the art that the methods and compositions of the present invention are useful in all plants and plant types wherein synthetic auxin mimics find utility.

Many of the crop plants with which the present invention can be practiced undergo four distinct drop periods during their yearly cycle. The first of these is the drop of flowers. This is followed by a drop occurring substantially simultaneously with fruit set. Subsequently, as the weather becomes warmer, most plants experience a June drop of fruit. The June drop is followed by a preharvest drop. The methods and compositions of the present invention can be used to control fruit and/or flower drop at one or more than one of the drop periods. In addition, the methods and compositions of the invention are useful for altering the natural timing of the drop. The alteration can either advance or retard the timing of the drop relative to the unaltered timing.

When the methods or compositions of the present invention are used to inhibit fruit and/or flower abscission, the canopy of the plant is preferably treated with a tryptophan compound at a time close to flowering. In a preferred embodiment, the plant is treated between 2 and 4 weeks prior to full bloom. In another embodiment, the plant is treated at full bloom. In yet another embodiment, the plant is treated at petal fall.

The plants can be treated once with the agent or can be treated repeatedly at intervals as necessary to elicit the desired response. When the tryptophan compound is applied to a plant more than once it is applied a selected number of times and at a frequency designed to produce the desired auxin response and the desired magnitude of auxin response in the plant. Thus, in one embodiment, the plant is treated between 1 and 10 times, typically between 1 and 5 times. Although, the plant can be treated at any convenient or effective interval, it will generally prove sufficient to treat the plant once every 1 to 4 weeks.

The methods of the present invention can be practiced in a number of plant growing environments including, for example, greenhouses, open fields, and orchards. The bulk amount of a composition of the invention which is applied will vary depending on the area to be covered, the amount of tryptophan compound to be administered and the effect it is desired to achieve. Thus, the following description is intended to be exemplary only and is not intended to limit the modes of application.

In one embodiment, the tryptophan compound is applied to an orchard of fruit trees or to vegetable crops. The tryptophan compound is applied, preferably by spraying, in an amount from about 5 gallons to about 1000 gallons per acre, more usually from about 10 gallons to about 800 gallons per acre. A typical orchard will have a density of trees of between about 100 to 144 trees per acre. When the compositions of the invention are used on orchards, the spraying rate is typically from about 50 gallons to about 1000 gallons per acre, preferably from about 200 gallons to about 600 gallons per acre. When vegetable crops are treated, the spraying rate is typically from about 5 gallons to about 200 gallons per acre, preferably from about 10 gallons to about 100 gallons per acre. Appropriate spraying apparatus, methods and amounts will be apparent to those of skill in the art.

In one embodiment of the invention, the tryptophan compound is used to prevent abscission of flowers and/or fruit and it is administered to the canopy of the plant at a concentration of from about $10^{-2}$ M to about $10^{-12}$ M, typically from about $10^{-8}$ M to about $10^{-10}$ M. In another embodiment, the tryptophan derivative acts as a thinning agent and promotes abscission. In this embodiment, the tryptophan derivative is applied to the canopy of the plant at a concentration of from about 1 M to about $10^{-8}$ M, typically from about $10^{-5}$ M to $10^{-7}$ M. These concentration ranges are offered as examples only and are not intended to limit the range of useful concentrations for tryptophan derivatives. The choice between these and other concentrations will be apparent to those of skill in the art or easily determined through routine experimentation.

The concentration of a particular tryptophan compound which is required to induce a response having the desired characteristics is dependent on a number of different factors. The relevant factors include, for example, the potency of the tryptophan compound, the number of repeat applications of the compound, the time of application relative to the plant's growth, flowering or fruiting cycle, the formulation in which the compound is administered and the purpose for which the compound is used. For example, when tryptophan is used to prevent fruit abscission in tomatoes, a concentration of $10^{-8}$ M was found to have the best effects. When tryptophan was with used with citrus at a higher concentration of $10^{-6}$ M, it acted to promote fruit abscission.

In a presently preferred embodiment, the tryptophan compound is used to inhibit fruit and or flower abscission and the plant is treated one or more times with a tryptophan compound at a concentration of from about $10^{-12}$ M to about $10^{-6}$ M, with the treatment beginning before the plant is in full bloom. In another preferred embodiment, the plant is treated as described above with the treatment beginning at the time the plant is in full bloom. In yet another preferred embodiment, the plant is treated as described above beginning after the plant has left full bloom. In still a further preferred embodiment, the plant is treated when it is in fruit.

In a second aspect, the invention is a method of controlling abscission in a living plant, the method comprising applying to the canopy of the plant an amount of tryptophan effective to control abscission. In a preferred embodiment of this aspect of the invention, the abscission which is controlled is that of buds, flowers, fruits and/or leaves. The control of the abscission can comprise either a reduction or an increase in abscission.

The embodiments of this aspect of the invention are generally similar to those described above in connection with the first aspect. For example, the timing of the tryptophan application is generally similar as are the solution concentrations, plant types and application amounts.

In a third aspect, the invention provides a method for decreasing acidity in citrus fruit comprising applying to the canopy of a plant an amount of a tryptophan compound effective to reduce the acidity, wherein the tryptophan compound has a structure according to Formula I. In this aspect, the acidity of the fruit is reduced, yet the sugar content either remains substantially unchanged or increases. As the acidity of treated fruit is reduced earlier in the year than untreated fruit, the fruit will taste sweeter earlier in the year than the fruit from untreated plants. The reduction in the time necessary to produce citrus fruit with a palatable sugar to acid balance allows the fruit to be harvested and brought to market earlier than the fruit from untreated plants.

The useful concentrations, application times and application iterations of the tryptophan compounds in the various embodiments of this aspect of the invention are substantially similar to those described above. In a presently preferred embodiment, tryptophan is used on citrus at a concentration of from about $10^{-8}$ M to about $10^{-10}$ M. In another preferred embodiment, tryptophan is applied to oranges at a concentration of approximately $10^{-8}$ M. In this embodiment, tryptophan is applied to the plant approximately 4 weeks after petal fall. For other plants, the appropriate concentration, application timing and application frequency of the tryptophan compound can be determined by routine experimentation on small populations of the plants of interest.

In a fourth aspect, the present invention provides a composition for application to crop plants comprising a productivity enhancing effective amount of compound having a structure

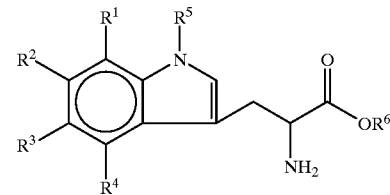

wherein
  $R^1$, $R^2$, $R^3$ and $R^4$ are independently members selected from the group consisting of hydrogen, hydroxyl, alkoxy, amino, halogen and $C_1$–$C_6$ alkyl; and
  $R^5$ and $R^6$ are independently members selected from the group consisting of hydrogen, $C_1$–$C_6$ alkyl, $C_1$–$C_6$ alkyl substituted with hydroxyl, polyalkylene glycol and substituted polyalkylene glycol.

In one embodiment, $R^1$, $R^2$, $R^3$ and $R^4$ are independently members selected from the group consisting of hydrogen, alkoxy and halogen;
  $R^5$ is a member selected from the group consisting of hydrogen and $C_1$–$C_2$ alkyl substituted with hydroxyl; and $R^6$ is a member selected from the group consisting of hydrogen, $C_1$–$C_2$ alkyl substituted with hydroxyl and polyalkylene glycol.

In another embodiment, $R^1$, $R^2$, $R^3$ and $R^4$ are independently members selected from the group consisting of hydrogen, methoxy and chloro;

$R^5$ is a member selected from the group consisting of hydrogen and $C_1$–$C_2$ alkyl substituted with hydroxyl; and $R^6$ is a member selected from the group consisting of hydrogen and polyalkylene glycol.

In a further embodiment, $R^1$, $R^2$, $R^3$ and $R^4$ are independently members selected from the group consisting of hydrogen and chloro;

$R^5$ is hydrogen; and $R^6$ is a member selected from the group consisting of hydrogen and polyalkylene glycol.

In a presently preferred embodiment, $R^1$–$R^6$ are hydrogen atoms and the compound of Formula I is tryptophan or an acceptable salt thereof.

The tryptophan compounds in the compositions of the invention can be utilized as pure enantiomers or mixtures of enantiomers in varying proportions including, but not limited to, a racemic mixture.

The methods and compositions of the invention can also incorporate additional compounds which promote or assist in the conversion of the tryptophan compound into a plant growth regulator such as indole acetic acid (IAA) or an analog thereof. An example of compounds which are known to enhance the biosynthesis of IAA from a tryptophan precursor are the gibberellins. See, for example, Law, *Physiol. Plantarum* 70:626–632 (1987). Thus, in one embodiment, the methods of the invention further comprise treating a plant with a gibberellin. The gibberellin can be administered to the plant simultaneously or non-simultaneously with the tryptophan compound. further, the gibberellin can be administered the same or a different number of times as the tryptophan compound. The gibberellin can be administered to the canopy of the plant or to the roots.

In another embodiment, the canopy of a plant is treated with a tryptophan compound in conjunction with a hormone such as a cytokinin (e.g., 6-benzyladenine) or an ethylene-releasing compound such as ethrel, ethephon, chlormequat and the like. The timing of the application for these compounds is similar the timing discussed above for the gibberellins.

In another embodiment, the compositions of the invention further comprise a gibberellin. Although the invention can be practiced with any gibberellin, preferred gibberellins include gibberellin $A_1$, gibberellin $A_3$ and gibberellin $A_4$. Other compounds which promote the biosynthesis of plant growth regulators from tryptophan compounds will be apparent to those of skill in the art.

Tryptophan compounds which comprise groups capable of enhancing the efficacy of the tryptophan compounds are also within the scope of the invention. As discussed above in the context of the methods of the invention, the efficacy of the tryptophan compounds can be improved by enhancing their uptake, and/or enhancing the intensity and/or duration of their action.

In still other embodiments, the compositions of the invention further comprise a cytokinin or an ethylene-releasing compound. In each of the above-described embodiments, the tryptophan compounds can be formulated, in the compositions of the invention, in conjunction with one or more gibberellins and/or cytokinins and/or ethylene-releasing compounds.

The compounds of the invention are applied to the canopy of plants according to the methods discussed above or other well known methods. The tryptophan compounds can be applied alone or in mixture with other plant hormones, fertilizers, pesticides or fungicides. The compositions can be applied in a mixture with a carrier or, if necessary, other auxiliary agents to form any one of the standard types of preparations commonly used in agriculture, for example, a dry blend, granules, a wettable powder, an emulsion, an aqueous solution and the like.

Suitable solid carriers are clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions can also be in the form of dispersible powders or grains, comprising, in addition to the tryptophan compounds, a surfactant to facilitate the dispersion of the powder or grains in liquid.

Liquid compositions include solutions, dispersions or emulsions containing the auxins together with one or more surface-active agents such as wetting agents, dispersing agents, emulsifying agents, or suspending agents. In those applications in which the compounds are applied as a foliar spray, surface active agents are preferably used.

Generally, any number of surfactants may be used consistent with the purpose of this constituent. For example the surfactant can comprise a nonionic, anionic, cationic, or zwitterionic surfactant. The surfactant can be present in the composition of the invention as formulated or, alternatively, the surfactants can be introduced during application to the plant. In such an instance, regardless of whether the application is conducted via automated or manual means, the surfactant can be combined with the composition of the invention prior to application or codispensed separately during application. The average molecular weight of useful surfactants ranges from about 100 to about 4000.

Cationic surfactants useful in compositions of the invention include, for example, amine ethoxylates, amine oxides, mono- and dialkylamines, imidazolinium derivatives, and alkylbenzyldimethylammonium halides.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds.

Anionic surfactants useful with the invention comprise, for example, alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention comprise α-N-alkylaminopropionic acids, n-alkyl-α-iminodipropionic acids, imidazoline carboxylates, amine oxides, sulfobetaines and sultaines.

Although the surfactant can be present in the composition in any useful amount, in preferred embodiments, it is present in an amount from about 0.1% to about 25%, more preferably from about 0.1% to about 10% and more preferably still from about 0.5% to about 5%. A surfactant is present in the compositions of the invention in a useful amount when it facilitates the dissolution of the tryptophan compound and/or enhances its uptake by the plant and/or its effectiveness in inducing the desired response.

In a preferred embodiment, the surfactant is a nonionic TWEEN® surfactant which is present in an amount from about 0.5% to about 5%. In a particularly preferred embodiment, the surfactant is TWEEN® 20 which is present in the composition in an amount from about 0.5% to about 5%.

The compositions of the invention can also contain suspending agents. Suitable suspending agents are, for example, hydrophilic colloids, for example polyvinylpyrrolidone and sodium carboxymethylcellulose, and the vegetable gums, for example, gum acacia and gum tragacanth.

Aqueous solutions, dispersions or emulsions may be prepared by dissolving the tryptophan compounds in water or an organic solvent which can, if desired, contain one or more surface active, sticking, wetting, dispersing, or emulsifying agents. Suitable organic solvents are, for example, alcohols, hydrocarbons, oils and sulfoxides. In embodiments using alcohols, methanol, isopropyl alcohol, propylene glycol and diacetone alcohol are preferred. In embodiments using oils, petroleum oils are preferred. Of the sulfoxides, dimethylsulfoxide is preferred.

The tryptophan compounds can also be formulated by microencapsulation. Microcapsules containing the desired tryptophan compound can be prepared by co-acervation; or, more preferably, by stirred interfacial polymerization of (for example) an isocyanate/diamine system. The resulting microcapsules may be used as an aqueous suspension.

The compositions which are to be used in the form of aqueous solutions, dispersions or emulsions are generally supplied in the form of a concentrate containing a high proportion of the tryptophan compounds, and the concentrate is then diluted with water before use. These concentrates are usually required to withstand storage for prolonged periods and after such storage, to be capable of dilution with water in order to form aqueous preparations which remain homogeneous for a sufficient time to enable them to be applied by conventional spray equipment. In general, concentrates can conveniently contain from 10–60 percent by weight of the tryptophan compounds. Dilute preparations ready for use may contain varying amounts of the tryptophan compounds, depending upon the purpose for which they are to be used, and a dilute preparation containing between $10^{-2}$ M and $10^{-12}$ M can normally be used.

In carrying out the methods of the invention, an "effective amount" of a tryptophan compound is applied to the plants. One of skill will recognize that an effective amount of a tryptophan compound will vary and will depend upon a number of factors including, for example, the particular formulation selected for use, the timing of the application, whether the compound is to be applied for leaf, flower or fruit uptake, the effect desired, and the plant species whose growth is to be regulated.

The compositions and methods of the invention can be used on a wide variety of plants. Exemplary plants include species from the genera Asparagus, Atropa, Avena, Brassica, Citrus, Citrullus, Capsicum, Cucumis, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Panieum, Persea, Pisum, Pyrus, Prunus, Raphanus, Secale, Senecio, Sinapis, Solanum, Sorghum, Trigonella, Triticum, Vigna, and, Zea.

The following examples are offered by way of illustrating the invention and are not intended to be limiting in any way.

EXAMPLES

The following examples illustrate the use of the methods and compositions of the invention. Example 1 demonstrates the ability of target organs to take up tryptophan which is applied to their surfaces. Further, the ability of plants to import tryptophan or its metabolites from the surface of their leaves and to convert the tryptophan to indole acetic acid (IAA) is confirmed and quantified. Example 2 details a field study which provided evidence that tryptophan, when applied via foliar application, is metabolically active.

Example 1

Example 1 illustrates laboratory experiments on the tryptophan uptake of several organs of the 'Washington' navel orange. The experiments utilized a radiolabeled tryptophan derivative to demonstrate that the organs were able to take up tryptophan and move it, or its metabolites, to other organs.

Laboratory Studies

Chemicals. Indole-3-pyruvic acid, indole-3-acetamide, indole-3-acetic acid, and DL-tryptophan were obtained from Sigma Chemical Corporation (St. Louis, Mo.). Solvents used in high performance liquid chromatography (HPLC) were HPLC grade from Fisher Scientific (Pittsburgh, Pa.). Radiolabeled L-[side chain 3-$^{14}$C]tryptophan, specific activity of 50 $\mu$Ci per ml, was obtained from American Radiolabeled Chemicals Inc. (Sommerville, N.J.). Liquiscint (liquid scintillation cocktail) was purchased from National Diagnostics (Atlanta, Ga.).

Uptake and transport of tryptophan. The ability of several organs of the 'Washington' navel orange (Citrus sinensis L. Osbeck) to take up L-[side chain 3-$^{14}$C]tryptophan applied to their surface was quantified in three separate experiments. In these experiments, movement of tryptophan, or its metabolite(s), to other organs was also examined. The analysis included: 1) tryptophan uptake by the flower petal and subsequent transport to the ovary; 2) tryptophan uptake by the fruit; 3) tryptophan uptake by the leaves and subsequent transport to the flowers; and 4) tryptophan uptake by the leaves and subsequent transport to the fruit. Branches were detached from 'Washington' navel orange trees located at the Citrus Research Center and Agricultural Experiment Station of University of California, Riverside. Stems of experimental shoots were quickly cut under distilled water and placed in distilled water in 200 ml Erlenmeyer flasks. When quantifying uptake by flower petals and movement into the ovary, a shoot bearing a single apical flower was used. Testing direct uptake by fruit was done using a shoot with a single apical fruit approximately 15 mm in transverse diameter. Shoots used to assess uptake by leaves and movement to flowers were trimmed to two flower buds at the elongate stage (approx. 2 cm long) in the uppermost position on the shoot; inflorescence leaves were removed. Shoots used to quantify uptake by leaves and movement into fruit were left with two fruit (10–12 mm transverse diameter) in apical positions. In each experiment, 500,000 dpm L-[side chain 3-$^{14}$C]tryptophan (55 nCi/nmol) was applied in 350 $\mu$l distilled water within a 12.5 mm diameter lanolin ring placed on the leaf tissue surface and 5 mm ring placed on the petal and fruit tissue surfaces. Shoots were transferred to a growth chamber and maintained at constant light for 12 hr at 24° C. and 12 hr at 19° C. After 48-hr, the appropriate organs were collected and those to which radioactivity had been applied were washed with 3 ml aliquots of distilled water until the radioactivity in the wash water was equal to background radioactivity. The organs were homogenized in 80% methanol with a Polytron tissue homogenizer (PCU-2, Brinkmann Instruments, Westbury, N.Y.) at speed 5. Samples were centrifuged at 15,000 rpm (26,900 g) for 20 minutes. The supernatant was decanted and concentrated to 150 μl in a Jouan RC-10 centrifugal vacuum concentrator (Jouan, Inc., Winchester, Va.), diluted with 2.5 ml Liquiscint and the amount of radioactivity in each sample determined by using a Beckman LS5000TD liquid scintillation spectrometer (Beckman Instruments, Irvine, Calif.). Quenching was determined by an automatic external standardization system of quench analysis. A standard quench curve was determined using a series of samples containing a known quantity of $^{14}C$ radioactivity and increasing amounts of chemical quencher.

Incorporation of L-[side chain 3-$^{14}C$]tryptophan into IAM, IPyA and IAA. Flowers, fruit (8–10 mm transverse diameter), and young fully expanded leaves of *C. sinensis* were used to assess the incorporation of L-[side chain 3-$^{14}C$]tryptophan into IAA in two separate experiments. All glassware, utensils, and plant material were rinsed with sterile water, immersed in 40% bleach for 10 minutes, and then rinsed with sterile distilled water. Under aseptic conditions, flowers cut into two pieces longitudinally, fruit cut into quarters, and leaves cut into 1×1-cm squares were transferred to nutrient agar and incubated at 30° C. for 72 hr both in the dark and in the light. Duplicate samples (500 mg fresh weight) of each tissue were transferred aseptically to 25 ml Erlenmeyer flasks containing 500,000 dpm L-[side chain 3-$^{14}C$]tryptophan (55 nCi/mol) in sterile 10 mM 2-[N-morpholino]ethanesulfonic acid (MES) buffer at a final volume of 5 ml, pH 6.5. Reaction mixtures were incubated for 16 hr in the dark at 30° C. in a water bath-shaker. At the end of the reaction period, the tissue pieces were removed from the incubation medium and washed three times with 1 ml of distilled water which was added to the medium. The samples of medium and tissue were freeze dried. Tissue was extracted in 80% methanol for 20 hr at 4° C. The extract was dried under vacuum in a Jouan RC-10 centrifugal concentrator. Samples were dissolved in 5 ml of 0.1M acetic acid and filtered through a preconditioned Waters SepPak C-18 cartridge. This eluent was dried under vacuum in a Jouan RC-10 concentrator and stored at −20° C. until analysis by HPLC.

Isolation of IAA, indole-3-acetamide (IAM) and indole-3-pyruvic acid (IPyA) in the processed samples was by reverse phase HPLC at room temperature through 9.4 mm×25 cm, 5 μm particle size Zorbax ODS column eluted with 10% aqueous methanol acidified with 2% formic acid (final conc.):methanol (70:30, by volume) at a flow rate of 1 ml per minute. IAA, IAM, and IPyA were detected at 254 nm at sensitivity of 0.04 absorbance units full scale. The retention times of authentic standards were as follows: IAM, 18.3–18.6 minutes; IPyA, 35.2–35.8 minutes; and IAA, 40.7–40.9 minutes. Fractions with these retention times were collected and purified further by rechromatographing as described above, three times for the IAM fraction and two times for the IAA and IPyA fractions. When only the IAA fraction was recovered, the ratio of acidified methanol-:methanol was 65:35 (by volume) to reduce elution times. The purified fractions were concentrated under vacuum to 150 μl and diluted with 2.5 ml Liquiscint. The content of radioactivity in each sample was determined as described above.

Results

Uptake and transport of L-[side chain 3-$^{14}C$]tryptophan by citrus leaves, flowers and fruit. All tissues of the 'Washington' nucellar navel orange tested were able to take up L-[side chain 3-$^{14}C$]tryptophan (Table 1). Direct application of tryptophan to the fruit resulted in the highest percentage uptake (7%). Application of tryptophan to the petal resulted in transport to the ovary. Uptake of tryptophan applied directly to leaves was relatively low (0.1%). The amount of tryptophan transported from leaves to fruit or flowers was similar, an average of 79 and 75 dpm per organ, respectively. Approximately one third, of the tryptophan taken up by leaves was transported to the two fruit or the two flowers residing at the apex of the shoots (Table 1).

TABLE 1

Uptake and transport of L-[side chain 3-$^{14}C$] tryptophan applied to the surface of leaves, fruit, and flowers of the 'Washington' nucellar navel orange during a 48-hr incubation period.

| Exp. number | tissue treated | | | | | |
|---|---|---|---|---|---|---|
| | petal | leaf(1) | leaf(1) | leaf(2) | leaf(2) | |
| | fruit | ovary | leaf(1) | fruit[y] | leaf(2) | flowers[y] |
| 1 | 43983 | 1087 | 723 | 345 | 384 | 105 |
| 2 | 24757 | 930 | 123 | 64 | 213 | 175 |
| 3 | 41870 | 602 | 100 | 62 | 568 | 168 |
| Average | 36870 | 873 | 315 | 157 | 388 | 149 |

[z]L-[side chain 3-$^{14}C$]tryptophan (5000,000 dpm; 55 nCi/nmol) was applied in 350 μL distilled water with a lanolin ring on the surface of fruit, petal and leaf (1) and (2) for a period of 48 hr at 24° C. for 12 hr and 19° C. for 12 hr under continuous light.
[y]Represents combined import of two organs.

Incorporation of radiolabled L-[side chain 3-$^{14}C$] tryptophan into IAM, IPyA, and IAA. In two separate experiments, tryptophan was incorporated into IAA by leaves, fruit, and flowers of the 'Washington' nucellar navel orange. More radiolabled IAA was consistently recovered from flower and leaf tissue than fruit (Table 2). Consistent with the synthesis of IAA from tryptophan, in three separate experiments, it was confirmed that leaves of the 'Washington' nucellar navel orange converted tryptophan to two putative intermediates in the pathway from tryptophan to IAA (Table 3). The lower amount of radiolabled IAA recovered from leaves reported in Table 3 relative to that reported in Table 2 is likely the result of the different conditions of recovery employed in the two studies and the repeated processing of the IAA fraction in the later study.

TABLE 2

Incorporation of L-[side chain 3-$^{14}C$]tryptophan into IAA by leaves, fruit, and flowers of the 'Washington' nucellar navel orange during a 16-hr incubation period at 30° C. under aseptic conditions.[z]

| | Incorporation of tryptophan into IAA by intact cells of citrus tissue | | | |
|---|---|---|---|---|
| | dpmg$^{-1}$ fresh wt:16h$^{-1}$ | | pmolg$^{-1}$ fresh wt:16h$^{-1}$ | |
| Tissue | Exp. 1 | Exp. 2 | Exp. 1 | Exp. 2 |
| leaf | 2754 | 2384 | 22.6 | 19.6 |
| fruit | 1732 | 1504 | 12.2 | 12.4 |
| flower | 2378 | 3124 | 19.4 | 25.6 |

[z]L-[side chain 3-$^{14}C$]tryptophan (500,000 dpm; 55 nCi/nmol) was provided in the incubation medium.

TABLE 3

Incorporation of L-[side chain $3-^{14}$C]tryptophan into indole-3-pyruvic acid (IPyA), indole-3-acetamide (IAM), and indole-3-acetic acid (IAA) by 'Washington' nucellar navel orange leaves during 16-hr incubation period at 30° C. under aseptic conditions.[z]

| Product | Incorporation of tryptophan into product | |
|---|---|---|
| | dpmg$^{-1}$ fresh wt:16h$^{-1}$ | pmolg$^{-1}$ fresh wt:16h$^{-1}$ |
| IPyA | 941 ± 156 | 7.6 |
| IAM | 1163 ± /101 | 9.5 |
| IAA | 234 ± 66 | 1.9 |

[z]L-[side chain 3-$^{14}$C]tryptophan (500,000 dpm; 55 nCi/nmol) was provided in the incubation medium. Results are means ±SE, n = 3 separate experiments.

To determine whether the metabolic conversions measured in the citrus tissue required intact cells, the capacity of homogenates of leaf, fruit, and flowers to convert tryptophan to IAA was assessed. Homogenization resulted in a 50% loss in capacity of leaf and flower tissue to convert tryptophan to IAA (Table 4 vs. Table 2). The capacity of intact cells of fruit to synthesize IAA was low (Table 2) and barely greater than that of homogenized fruit tissue (Table 4). The possibility that the incorporation observed reflected the activity of fungal or bacterial contamination of the navel orange tissues is considered unlikely because no growth of microorganisms was detected after incubation of leaf, flower, or fruit tissues or their homogenates on nutrient-rich agar either in the dark or light for 72 hr at 30° C.

TABLE 4

Incorporation of L-[side chain 3-$^{14}$C] tryptophan into IAA by homogenates of leaves, fruit, and flowers of the 'Washington' nucellar navel orange during a 16-hr incubation period at 30° C. under aseptic conditions.[z]

| Tissue | Incorporation of tryptophan into IAA by homogenized citrus tissue | | | |
|---|---|---|---|---|
| | dpmg$^{-1}$ fresh wt:16h$^{-1}$ | | pmolg$^{-1}$ fresh wt:16h$^{-1}$ | |
| | Exp. 1 | Exp. 2 | Exp. 1 | Exp. 2 |
| leaf | 1368 | 1250 | 11.2 | 10.2 |
| fruit | 1604 | 1174 | 13.1 | 9.6 |
| flower | 840 | 1670 | 6.9 | 13.6 |

[z]L-[side chain 3-$^{14}$C]tryptophan (500,000 dpm; 55 nCi/nmol) was provided in the incubation medium.

Example 2

Example 2 illustrates a field study designed to assess the effects of tryptophan application on peel thickness, juice content and fruit acidity. The study demonstrated that there were no adverse impacts on the plant characteristics examined. Surprisingly, the fruit from plants which were treated with tryptophan had a significantly lower acid content than juice from fruit which was not treated.

Field Study

The research trees were 20-year-old 'Washington' nucellar navel orange scion on 'Troyer' citrange rootstock (*C. sinensis* 'Washington'×*Poncirus trifoliata* L. Raf.) owned by Kings River Packing Company, Sanger, Calif. Tree density was 75 trees per acre; trees were hedged and skirted. The experimental design was completely randomized with 20 individual branch replicates per treatment. Branches were selected at approximately 1.2 m height on the south side of the tree and tagged to give samples with approximately 200 flowers per branch. There were six treatments: 1) control, no tryptophan spray; (2) $10^{-6}$ M DL-tryptophan applied at full bloom (Apr. 19, 1996); (3) $10^{-8}$ M DL-tryptophan applied at full bloom; (4) $10^{-10}$ M DL-tryptophan applied at full bloom; (5) $10^{-8}$ M DL-tryptophan applied two weeks after full bloom; (6) $10^{-10}$ M DL-tryptophan applied at full bloom and every two weeks for a total of 10 weeks (5 applications). Treatment sprays contained 1% TWEEN 20 surfactant and were applied to branches to the drip point. The number of fruit per branch and the size of their transverse diameter was determined after the end of the June drop period (Jul. 16, 1996), preharvest (Sep. 4, 1996), and at harvest (Jan. 17, 1997). Peel thickness, fruit weight, soluble solids, and percent acid were determined at harvest. Collected fruit were divided into replications of 8 fruit each. These replications were mechanically juiced, the amount of soluble solids present was assessed using a refractometer, and the percent acid was determined by titration to pH 8.2±0.1 with NaOH.

Results

Figure 2:
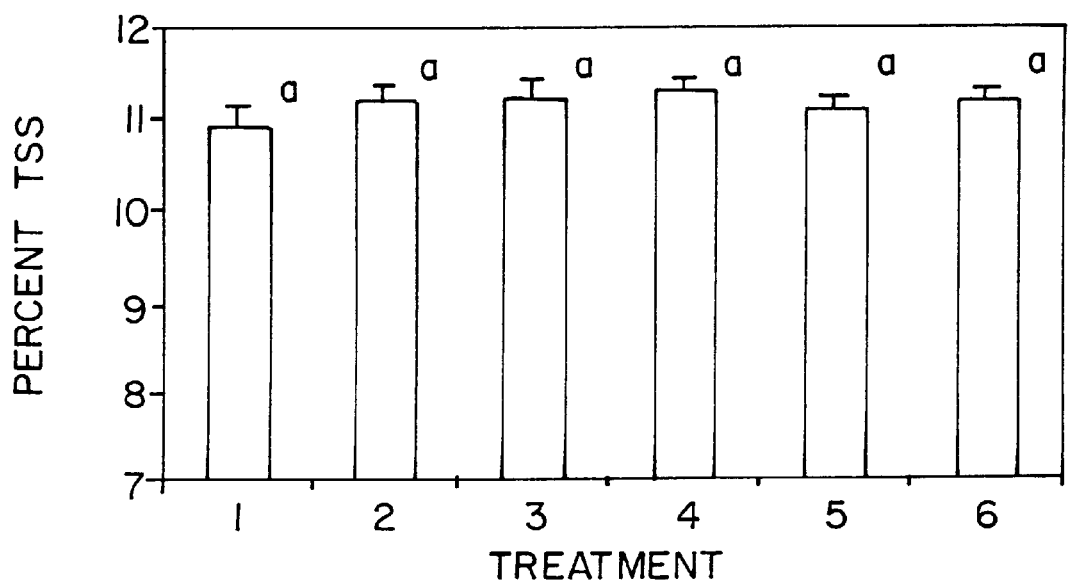
FIG. 2 shows the effect of foliar-applied DL-tryptophan on total soluble solids (TSS) of the juice at harvest. 1) control—no tryptophan; 2) $10^{-6}$ M tryptophan applied at fb; 3) $10^{-8}$ M tryptophan applied at fb; 4) $10^{-10}$ M tryptophan applied at fb; 5) $10^{-8}$ M tryptophan applied 2 was after fb; 6) $10^{-10}$ M tryptophan applied at fb+every 2 weeks for 10 weeks. (fb=full bloom). Error bars indicate the SE of the mean for 5 replicates for treatment 1; 6 replicates for treatments 2, 3, 5, and 6; and 8 replicates for treatment 5. The means were separated at p=0.10 using pairwise t-test.
Figure 3:
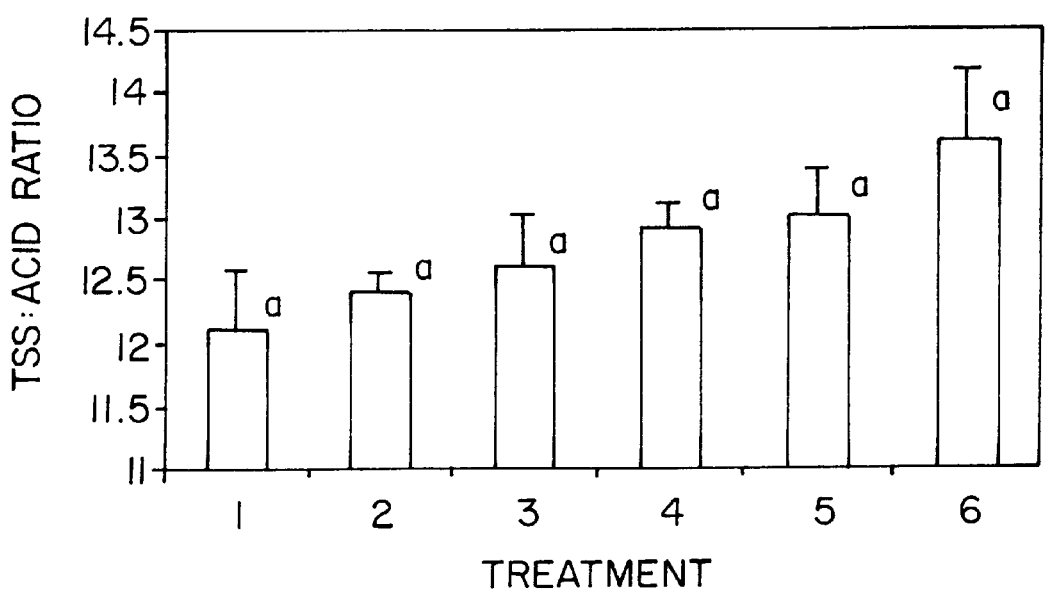
FIG. 3 shows the effect of foliar-applied DL-tryptophan on total soluble solids (TSS):acid ratio of the juice at harvest. 1) control—no tryptophan; 2) $10^{-6}$ M tryptophan applied at fb; 3) $10^{-8}$ M tryptophan applied at fb; 4) $10^{-10}$ M tryptophan applied at fb; 5) $10^{-8}$ M tryptophan applied 2 was after fb; 6) $10^{-10}$ M tryptophan applied at fb+every 2 weeks for 10 weeks. (fb=full bloom). Error bars indicate the SE of the mean for 5 replicates for treatment 1; 6 replicates for treatments 2, 3, 5, and 6; and 8 replicates for treatment 5. The means were separated at p=0.10 using pairwise t-test.

The tryptophan treatments had no effect on peel thickness or juice content. Across all parameters measured there were no negative effects resulting from any of the foliar-applications of DL-tryptophan. Visual assessment of the fruit revealed no changes in rind quality or color. A statistically significant decrease in the acid content of the juice was obtained using the lower concentrations ($10^{-8}$ M or $10^{-10}$ M) of DL-tryptophan applied after full bloom, especially multiple applications of $10^{-10}$ M DL-tryptophan (treatment 6, FIG. 1) (p=0.056). The DL-tryptophan treatments had no effect on the total soluble solids content of the juice (FIG. 2). Despite the significant decrease in percent acid with the two DL-tryptophan treatments made after full bloom, there was no statistically significant increase in total soluble solids:acid ratio (FIG. 3).

Example 3

Example 3 illustrates laboratory experiments on the tryptophan uptake of several organs of the 'Supersweet' tomato. The experiment was substantially similar to that described in Example 1 and utilized a radiolabeled tryptophan derivative to demonstrate that the organs were able to take up tryptophan and convert it to IAA. In two separate experiments, tryptophan was incorporated into IAA by leaves, flowers, and fruit of "Supersweet" tomato. The results of these experiments are displayed in Table 5.

To determine whether the metabolic conversions measured in the tomato tissue required intact cells, the capacity of homogenates of leaf, fruit and flowers to convert tryptophan to IAA was assessed. In two separate experiments homogenization of the tissues resulted in a 30%–50% loss in the capacity of leaves, flowers and fruit to convert tryptophan to IAA. The possibility that the incorporation observed reflected the activity of fungal or bacterial contamination of the tomato tissues is considered unlikely. No growth of microorganisms was detected after incubation of leaf, flower or fruit tissues, or their homogenates, on nutrient-rich agar either in the dark or light for 72 h at 30° C. L-[side chain 3-$^{14}$C]tryptophan (500,000 dpm; 55 nCi/nmol) was provided in the incubation medium.

TABLE 5

Incorporation of L-[side chain 3-$^{14}$C]tryptophan
into IAA by leaves, fruit, and flowers of 'Supersweet' tomato
during a 16-hr incubation period at 30° C. under aseptic conditions.$^z$

| | Incorporation of tryptophan into IAA by intact cells of tomato tissue | | | |
|---|---|---|---|---|
| | dpmg$^{-1}$ fresh wt:16h$^{-1}$ | | pmolg$^{-1}$ fresh wt:16h$^{-1}$ | |
| Tissue | Exp. 1 | Exp. 2 | Exp. 1 | Exp. 2 |
| leaf | 971 | 981 | 3.9 | 3.9 |
| fruit | 1206 | 645 | 48.3 | 2.6 |
| flower | 391 | 725 | 1.6 | 2.9 |

Example 4

Example 4 demonstrates the effectiveness of a foliar spray of DL-tryptophan on increasing the yield of mature fruit of 'Supersweet' tomato. The experiment utilized two applications of a 10$^{-8}$ M solution of DL-tryptophan. The first application occurred at the first major full bloom. The second application followed two weeks after this full bloom. The yield is from three harvests occurring 1 month after the last treatment and every three weeks thereafter for the two additional harvests. The results are summarized in Table 6.

TABLE 6

Effect of foliar-applied DL-tryptophan
on yield of mature edible fruit of 'Supersweet' tomato

| Treatment | Yield (g/plant) | No. of fruit/plant | fruit wt. (g/fruit) |
|---|---|---|---|
| 10$^{-8}$ M DL-tryptophan | 474 | 61 | 7.8 |
| Control (no tryptophan) | 304 | 50 | 6.1 |
| P value | 0.05 | 0.09 | NS |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of enhancing the productivity of a living, intact crop plant, the method comprising applying to the canopy of said plant an amount of a compound effective in enhancing said productivity, said compound having the structure:

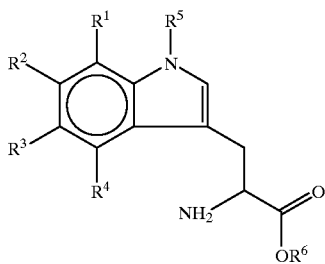

wherein
$R^1$, $R^2$, $R^3$ and $R^4$ are independently members selected from the group consisting of hydrogen, hydroxyl, alkoxy, amino, halogen and $C_1$–$C_6$ alkyl;
$R^5$ and $R^6$ are independently members selected from the group consisting of hydrogen, $C_1$–$C_6$ alkyl, $C_1$–$C_6$ alkyl substituted with hydroxyl, polyalkylene glycol and substituted polyalkylene glycol.

2. A method according to claim 1, wherein $R^1$, $R^2$, $R^3$ and $R^4$ are independently members selected from the group consisting of hydrogen, alkoxy and halogen;
$R^5$ is a member selected from the group consisting of hydrogen and $C_1$–$C_2$ alkyl substituted with hydroxyl; and
$R^6$ is a member selected from the group consisting of hydrogen, $C_1$–$C_2$ alkyl substituted with hydroxyl and polyalkylene glycol.

3. A method according to claim 2, wherein $R^1$, $R^2$, $R^3$ and $R^4$ are independently members selected from the group consisting of hydrogen, methoxy and chloro;
$R^5$ is a member selected from the group consisting of hydrogen and $C_1$–$C_2$ alkyl substituted with hydroxyl; and
$R^6$ is a member selected from the group consisting of hydrogen and polyalkylene glycol.

4. A method according to claim 3, wherein $R^1$, $R^2$, $R^3$ and $R^4$ are independently members selected from the group consisting of hydrogen and chloro;
$R^5$ is hydrogen; and
$R^6$ is a member selected from the group consisting of hydrogen and polyalkylene glycol.

5. The method of claim 3, wherein $R^1$, $R^2$, $R^3$, $R^4$, $R^5$ and $R^6$ are H.

6. The method of claim 1, wherein the auxin response is the control of abscission.

7. The method of claim 1, wherein the auxin response is enhanced fruit set.

8. The method according to claim 6, wherein the plant is a member chosen from the group consisting of citrus, avocado and tomato.

9. The method according to claim 8, wherein the citrus plant is an orange.

10. A method of controlling abscission in a living, intact plant, said method comprising applying to the canopy of said plant, an amount of tryptophan effective to control abscission.

11. The method of claim 10, wherein the abscission is of an organ selected from the group consisting of buds, flowers, fruits and leaves.

12. The method of claim 11, wherein said abscission is reduced.

13. The method of claim 11, wherein said abscission is enhanced.

14. The method of claim 10, wherein said tryptophan is applied before said plant is in full bloom.

15. The method of claim 10, wherein said tryptophan is applied when said plant is in full bloom.

16. The method of claim 10, wherein said tryptophan is applied after said plant is in full bloom.

17. The method of claim 10, wherein said tryptophan is applied after said plant is in fruit.

18. The method of claim 12, wherein said tryptophan is applied at a concentration of between 10$^{-2}$ M and 10$^{-12}$ M.

19. The method of claim 18, wherein said tryptophan is applied at a concentration of between 10$^{-8}$ M and 10$^{-10}$ M.

20. The method of claim 13, wherein said tryptophan is applied at a concentration of between 1 M and 10$^{-8}$ M.

21. The method of claim 20, wherein said tryptophan is applied at a concentration of between 10$^{-5}$ M and 10$^{-7}$ M.

22. The method of claim 10, wherein said plant is a member selected from the group consisting of citrus, tomato and avocado.

* * * * *